ID-No. Field of search...

United States Patent [19]

Boyajian

[11] 4,261,744
[45] Apr. 14, 1981

[54] PALLADIUM-BASED DENTAL ALLOY CONTAINING INDIUM AND TIN

[76] Inventor: Ben K. Boyajian, Chemodent, P.O. Box 7787, Charlottesville, Va. 22906

[21] Appl. No.: 83,344

[22] Filed: Oct. 10, 1979

[51] Int. Cl.³ .......................... C22C 5/02; C22C 5/06
[52] U.S. Cl. ................................. 75/172 R; 433/200; 433/207
[58] Field of Search .......................... 75/172 R; 32/8; 433/199, 200

[56] References Cited

U.S. PATENT DOCUMENTS

| 2,074,996 | 3/1937 | Cohn | 75/122 |
|---|---|---|---|
| 2,105,312 | 1/1938 | Cohn | 75/172 |
| 2,781,580 | 2/1957 | Liebig | 32/5 |
| 3,819,366 | 6/1974 | Katz | 75/172 R |
| 3,928,913 | 12/1975 | Schaffer | 32/8 |
| 3,929,474 | 12/1975 | Ingersoll | 75/122 G |
| 3,929,475 | 12/1975 | Ingersoll | 75/173 R |
| 3,961,420 | 6/1976 | Tuccillo | 32/5 |
| 4,124,382 | 11/1978 | Prosen | 75/172 R |

OTHER PUBLICATIONS

Kosovinc et al., Metall, 26, (9), (1972), 917–920.

Primary Examiner—L. Dewayne Rutledge
Assistant Examiner—Upendra Roy
Attorney, Agent, or Firm—Charlotte M. Kraebel

[57] ABSTRACT

A non-discoloring palladium-based alloy, free of silver or gold, suitable for fusion to dental porcelain compositions consists essentially of 75–85% by weight of Pd, 5–10% by weight of In, 5–10.5% by weight of Sn, up to 7.5% by weight of Co, Cr or Ni and up to 0.25% by weight of Si.

8 Claims, No Drawings

# PALLADIUM-BASED DENTAL ALLOY CONTAINING INDIUM AND TIN

PRIOR ART STATEMENT

Fusion of dental porcelain to metal frames has been common practices for the past twenty years. Gold, alloyed with platinum, palladium, silver and minor base elements, was conventionally the primary frame component.

As gold prices have climbed, researchers and practitioners sought alternatives to gold. One approach was lowering the gold content and adding more palladium and/or silver; another was the use of non-precious metals, such as nickel-chrome alloys or cobalt-based alloys. Although non-precious metal alloys are widely used, their acceptability is limited by poor bond strength to porcelain and nickel sensitivity of many patients.

Another approach has been the use of palladium-silver alloys. These alloys have had limited acceptance because silver discolors porcelain dental fittings. Consequently, even minor amounts of silver are no longer used.

The use of a high Pd or Pd-Pt based dental casting alloy containing as non-precious components a major amount of Co and Co-Ni and minor amounts In or Sn is disclosed by Schaffer in U.S. Pat. No. 3,928,913. Although these alloys can be pickled with HCl to a white coloration, the normal color of oxide-coated alloy workpieces is gray. It will be apparent that discoloration can occur under thin areas of porcelain at the marginal region of a tooth and that the discoloration is aesthetically unacceptable. Moreover, even when a dark-appearing alloy inside of a tooth will be covered with cement, many dentists prefer to work with alloys which are light in appearance. These alloys are generally harder than A.D.A. Type IV alloys and are therefore difficult to cut and grind. In addition, the alloys described by Schaffer tend to absorb gases and produce highly porous castings.

The use of high concentrations of Pd in alloys for dental applications is disclosed by Chon in U.S. Pat. Nos. 2,074,996 and 2,105,312 and by Prosen in U.S. Pat. No. 4,124,382. Cohn discloses Ni, to a maximum of 9%, and Ru, to a maximum of 9%, as alloying elements. Prosen indicates the use of Sn, Fe, Al, and B as required additives and of Ru as an optional additive.

Alloys containing Au or Ag, in addition to Pd, are set forth in the following U.S. Pat. Nos.: 1,999,866 Capillon et al, 3,424,577 Neilson et al, 3,574,611 Prosen, 3,679,402 Hirschhorn, 3,819,366 Katz, 3,929,474 Ingersoll, 3,929,475 Ingersoll, 3,961,420 Tuccillo, 3,981,723 Tuccillo, 4,008,080 Wagner, 4,123,262 Cascone.

It is apparent that there is a continuing need for low cost gold-free alloys, which do not discolor because of their silver content, which are easy to fabricate and which are compatible with and adhere firmly to porcelain formulations used in dental prostheses.

OBJECT OF THE INVENTION

It is an object of the invention to provide a palladium alloy, containing neither silver nor gold, which has the properties of an alloy of high nobility but is much lower in cost than a gold-based alloy. Because palladium costs about half of what gold costs in present day markets and is much lower in density than gold, the alloys of the invention provide a significant economic advantage over gold without loss of desired characteristics.

SUMMARY OF THE INVENTION

In a compositional aspect this invention relates to an alloy consisting essentially of 75–85% by weight of Pd, 5–10.5% by weight of In, 5–10.5% by weight of Sn, up to 7.5% by weight of Co, Cr or Ni and up to 0.25% by weight of Si.

In a clinical aspect, this invention relates to a dental prosthesis comprising a cast palladium alloy base, the alloy consisting essentially of 77–82% by weight of Pd, 7.5–10.5% by weight of In, 7.0–10.0% by weight of Sn, 1.0–7.5% by weight of Co and 0.1–0.25% by weight of Si, in the shape of a tooth and a porcelain coating firmly adhered to at least a portion of the cast palladium alloy base.

DETAILED DESCRIPTION

Alloys are made by combining the weighed metallic components in a crucible and melting in a vacuum furnace. The molten material is held in the liquid state for an hour or more and then cooled rapidly at a rate of about 100° F./min (55° C./min) to room temperature. The product is in the form of ingots.

Preferably, the alloys of this invention will contain Pd, In, Sn, Co and at least 0.01% by weight of Si. More preferably, the Pd content is 77–82% by weight. More preferably, the alloys contain 77–82% by weight of Pd, about 7.5% by weight of In, above 7.0% by weight of Sn and more than 0.1% by weight of Si. Alloys of the foregoing compositions may be used for routine crown and bridge work, generally including full cast crowns and onlays, as well as for bonding to procelain prostheses. However, alloys particularly adapted for bonding to porcelain will contain at least 1.0%, preferably 4.0% by weight of Co to assure adequate hardness. Hardness was determined by the Vickers microhardness test, also known as the Diamond Hardness Test (DPN).

Alloys made in accordance with the invention melt in the range below 1375° C., but the preferred alloys melt at 1150–1375° C. and have a coefficient of thermal expansion compatible with that of procelain used for dental restoration or prosthesis, which is generally $14–16 \times 10^{-6}$%/°C. to 600° C.

It will be understood that, although the coefficient of thermal expansion of the alloys of this invention can be measured by dilatometry, there is not inevitably an exact correlation between the measured coefficient of thermal expansion and behavior in a dental laboratory. Accordingly, the following qualitative criteria can be used as a practical test of compatibility between the alloy and the porcelain of a dental prosthesis:

(1) no porcelain cracking is observed as a result of cooling the prosthesis from the fusion temperature or of refiring the prosthesis
(2) no cracks are observed around small or large pontics
(3) no cracks are observed in any single unit or multiple unit splint, including a full arch splint of 14 teeth
(4) no cracks occur upon repeated refiring
(5) no cracks occur as a result of heavy grinding of the porcelain
(6) no cracks occur upon post-soldering of the prosthesis
(7) no cracks occur following hard tapping of the prosthesis with a metal instrument, e.g., a hammer.

Addition of silicon to the alloys of this invention decreases absorption of gases by the molten alloy and, at the preferred levels of 0.10-0.25% by weight of Si, completely prevents gas absorption. The resulting alloys are not porous because of gases trapped therein and adhere more firmly to dental porcelain than porous alloys. However, inclusion of more than 0.25% by weight of Si in the alloys produces a cast product which contains cracks and voids.

In addition to their superiority in appearance over dark-appearing alloys containing silver or high amounts of non-precious metals, the alloys of the present invention permit oxide formation sufficient to attain good bonding to porcelain, but low enough to avoid weakening encountered at high oxide levels.

The porcelains which can be bonded to the alloys of this invention are, for example, those based on feldspar, nepheline or a crystalline constituent of leucite, as disclosed by Schaffer, supra, incorporated herein by reference. It will be understood that any porcelain having a coefficient of thermal expansion about the same as the alloy being employed can be used.

A technique suitable for making dental restorations is described in Tucillo U.S. Pat. No. 3,961,420, supra, incorporated herein by reference. As indicated by the Tucillo reference, "compatibility" between alloy and porcelain means that each has essentially matching coefficients of thermal expansion, that of the porcelain preferably being slightly less than that of the alloy. In using the alloys of this invention, a slightly broader opaque firing range can be used, between about 955°-1010° C.

Alloys of this invention become firmly bonded to the porcelain portion of the reconstruction during the heat treatment, preferably by chemical and diffusion bonding.

The alloys of this invention have properties meeting criteria for bridgework, defined by ADA specification no. 5, Types III and IV. Generally, alloys containing higher amounts of Co, above about 4.0%, meet type IV standards. Alloys of this type can be used for long span bridgework, of five units or above.

DESCRIPTION OF PREFERRED EMBODIMENTS

For general use, preferred alloys are those consisting essentially of 77-82% by weight of Pd, 7.5-10.5% by weight of In, 7.0-10.5% by weight of Sn, up to 7.5% by weight of Co and 0.1-0.25% by weight of Si, and having a melting point of 1150°-1375° C.

For use in dental restorations, preferred alloys consist essentially of 77-82% by weight of Pd, 7.5-10.5% by weight of In, 7.0-10.0% by weight of Sn, 4.0-7.5% by weight of Co and 0.1-0.25% by weight of Si and have a melting point of 1150°-1375° C. In a most preferred embodiment, the prosthesis will be made of the corresponding alloys, the porcelain coating being firmly adhered to the alloy by chemical and diffusion bonding.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius, unless otherwise indicated all parts and percentages are by weight.

EXAMPLES 1-7

Alloys of the compositions indicated below were made by combining the indicated components in a crucible and melting in a vacuum furnace at about 1400° C. The melt was kept in the liquid state for about an hour and poured into ingot molds which were cooled at a rate of about 55° C./min to give ingots. Properties of the products are given in the Table below:

| Example | % by weight | | | | | Properties | |
| | Pd | In | Sn | Co | Si | Vickers (DPN) | ADA type |
| --- | --- | --- | --- | --- | --- | --- | --- |
| (1) | 78.2 | 8.9 | 7.7 | 5.0 | .2 | 181 | IV |
| (2) | 79.5 | 8.4 | 8.4 | 3.5 | .2 | 140 | III |
| (3) | 80.2 | 9.1 | 9.0 | 1.5 | .2 | 115 | III |
| (4) | 81.9 | 7.8 | 10.2 | 0 | .1 | 89 | |
| (5) | 78.9 | 8.6 | 7.8 | 4.5 | .2 | 176 | IV |
| (6) | 77.2 | 8.9 | 7.7 | 6.0 | .2 | 192 | IV |
| (7) | 77.0 | 9.0 | 7.1 | 6.7 | .2 | 198 | IV |

The alloy containing no Co (Example 4) was relatively softer than the others and was judged unsuitable for use in porcelain-alloy restorations. It is useful for onlays and routine crown and bridge work.

Any of the other alloys was judged acceptable for use in porcelain-alloy prosthesis, but those containing more than about 4.0% by weight of Co and being of A.D.A. Type IV (Examples 1, 5, 6 and 7) are preferred for this purpose.

EXAMPLE 8

The alloy of Example 1 is fabricated into a tooth restoration as described by Tucillo U.S. Pat. No. 3,961,420, using a temperature of 955°-1010° C. for the opaquing step. The porcelain employed was Vita, obtained from Unitek Corporation, 2724 South Peck Road, Monrovia, California 91016.

An acceptable restoration was obtained, that is, the bonding was well opaqued and no bubble formation was noted. No crazing or blistering of the porcelain was observed. The prosthesis had the same attributes as a restoration made from porcelain and gold alloys.

EXAMPLE 9

Alloy prepared as in Example 5 was used to prepare a tooth restoration containing an alloy based in the shape of a tooth, firmly bonded to Vita porcelain. The restoration was acceptable to the dental trade, compatibility between the alloy and porcelain meeting the criteria described above.

EXAMPLE 10

Alloys are prepared as in Example 1, substituting Ni or Cr for Co. The properties of the alloys obtained are similar to those of the alloys containing Co.

The preceeding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A gold-free, silver-free alloy consisting essentially of 75–85% by weight of Pd, 5–10.5% by weight of In, 5–10.5% by weight of Sn, 1.0–7.5% by weight of Co and 0.1–0.25% by weight of Si.

2. The alloy of claim 1, consisting essentially of 77–82% by weight of Pd, 5–10.5% by weight of In, 5–10.5% by weight of Sn, 1.0–7.5% by weight of Co and 0.1–0.25% by weight of Si.

3. The alloy of claim 1, which contains at least 4.0% by weight of Co.

4. The alloy of claim 1, consisting essentially of 77–82% by weight of Pd, 7.5–10.5% by weight of In, 7.0–10.5% by weight of Sn, 1.0–7.5% by weight of Co and 0.1–0.25% by weight of Si.

5. The alloy of claim 1, consisting essentially of 77–82% by weight of Pd, 7.5–10.5% by weight of In, 7.0–10.0% by weight of Sn, 1.0–7.5% by weight of Co and 0.1–0.25% by weight of Si.

6. The alloy of claim 1, consisting essentially of 77–82% by weight of Pd, 7.5–10.5% by weight of In, 7.0–10.0% by weight of Sn, 4.0–7.5% by weight of Co and 0.1–0.25% by weight of Si.

7. A dental prosthesis comprising a cast palladium alloy base in the shape of a tooth, the palladium alloy being that of claim 5, and a porcelain coating firmly adhered to at least a portion of the cast palladium alloy base.

8. The dental prosthesis of claim 7, wherein the cast alloy consists essentially of 77–82% by weight of Pd, 7.5–10.5% by weight of In, 7.0–10.0% by weight of Sn, 4.0–7.5% by weight of Co and 0.1–0.25% by weight of Si and the porcelain coating is firmly adhered to the cast palladium alloy base by chemical and diffusion bonding.

* * * * *